US00PP10572P

United States Patent [19]

Fruehwirth

[11] Patent Number: Plant 10,572

[45] Date of Patent: Aug. 25, 1998

[54] POINSETTIA PLANT 'BRIGHT RED FREEDOM'

[75] Inventor: Franz Fruehwirth, Encinitas, Calif.

[73] Assignee: Paul Ecke Ranch, Inc., Encinitas, Calif.

[21] Appl. No.: 829,177

[22] Filed: Mar. 31, 1997

[51] Int. Cl.[6] ..... A01H 5/00

[52] U.S. Cl. ..... Plt./86.4

[58] Field of Search ..... Plt./86.4

*Primary Examiner*—James R. Feyrer
*Assistant Examiner*—Melissa L. Kimball
*Attorney, Agent, or Firm*—Arnold, White & Durkee

[57] ABSTRACT

Poinsettia "Bright Red Freedom" is a new cultivar, distinguished by bright red flower bracts, early flowering and self-branching characteristics. "Bright Red Freedom" is a naturally occurring sport of the poinsettia "490" (U.S. Plant Pat. No. 7,825) with the same cultural requirements. The new poinsettia produces a very desirable, early flowering, branched pot plant with bright red flower bracts that do not look "dull" under interior lighting.

1 Drawing Sheet

BACKGROUND OF THE NEW PLANT

This new poinsettia cultivar, "Bright Red Freedom," originated as a natural bright red bracted sport of poinsettia "490" (U.S. Plant Pat. No. 7,825) among several thousand plants of "490" in my greenhouse in Encinitas, Calif. It was selected in November 1996 because of its early flowering, bright red flower bracts and self branching characteristics; traits which distinguish it from other poinsettia cultivars, and make it a desirable plant for commercial greenhouse production. The bright red flower bracts of this new sport, "Bright Red Freedom", make a more impressive display in retail stores and homes where it retains the bright red bract color. The dark red bract color of the parent "490" often looks dull under interior lighting. The new sport retains the same desirable dark green foliage as the parent. Otherwise, "Bright Red Freedom" had the same characteristics and cultural requirements as its parent, "490".

After selection, "Bright Red Freedom" was vegetatively reproduced from stem cuttings for test purposes in Encinitas, Calif. By subjecting clones of this plant to successive generations of vegetative propagation, it was demonstrated that the distinctive characteristics of "Bright Red Freedom" held true from generation to generation.

DESCRIPTION OF THE PHOTOGRAPHS

Poinsettia "Bright Red Freedom" is illustrated in the accompanying color photographs. The upper photo is a side view of 3 single stem plants per pot in full flower.

The lower photo is a top view of the same plants showing flower and bract formation.

DESCRIPTION OF THE PLANT

The following is a detailed description of this new poinsettia as observed in Encinitas, Calif., U.S.A. during December 1996. Observations were recorded from flowering plants, grown as 3 single stem plants per pot. The pot was 14 cm. in diameter and 11 cm. in height. Color designations are compared to the 1986 edition of R.H.S. Colour Chart, first published in 1966 by The Royal Horticultural Society, London England.

THE PLANT

The following chart summarizes the differences between Poinsettia "Bright Red Freedom" and its parent plant "490" (PP No. 7825).

| | "Bright Red Freedom" | "490" |
|---|---|---|
| Flower bract color | | |
| Upper surface | RHS 45A-B | RHS 46A-B |
| Under surface | RHS 47B | RHS 53B-C |
| Cyathium | Green, fringed light red | Green, fringed dark red |

Origin: Naturally occurring sport of Poinsettia "490" (U.S. Plant Pat. No. 7,825).

Classification:

*Botanic.*—Euphorbia pulcherrima Willd.

*Common name.*—Poinsettia.

*Cultivar name.*—"Bright Red Freedom".

Form: Shrub.

Height: Short.

Growth habit: As a single stemmed plant, upright with self-branching side shoot. The application of a chemical growth retardant may not be needed to restrict height for commercial pot plant production. I observed 3 unpinched plants in a pot with an overall height of 34 cm and an overall width of 41 cm. The bract diameter of individual flowers was 31 cm.

Branching: Axillary branches will develop and terminate in a flower without pinching. However, it is usually desirable to pinch "Bright Red Freedom" before flower induction and remove all terminal dominance. Then, all axillary branches will develop uniformly and at a faster rate.

Growth rate: Rooting of stem cuttings occurs in 12–18 days under intermittent mist. The plant will flower in about eight weeks under continuous long night conditions and night temperatures of about 16–18 degrees C. In my greenhouse, poinsettia "Bright Red Freedom" reached full maturity on November 20, the same date as its parent, poinsettia "490".

Foliage: The foliage is clean and uniformly dark green from bottom to top of the plant. The leaves are of medium size, leaf blades typically being 13 cm. long and about 10 cm. wide with leaf petioles 6 cm. long.

*Leaf shape.*—Typical leaves are generally ovate with acute to obtuse bases and acuminate tips. Leaf margins are usually entire with a few leaves slightly lobed with one small indentation on one or both sides of the leaf blade.

*Leaf surface.*—Upper surface — Smooth and glabrous. Under surface — Finely pubescent.

*Color.*—Upper side — Green, much darker than R.H.S. 139A. Under side — Green, between R.H.S. 147A-B.

*Retention.*—The foliage lasts extremely well even under low light intensities in the consumer's home.

Bracts: Generally there were 18–24 bright red bracts of various sizes subtending the cyathia. The primary bracts are large, have blades typically 16–18 cm. long and 10–11 cm. wide with petioles 4 cm. long.

*Shape.*—Primary bracts are ovate with acute bases and acuminate tips. Primary bracts are lobed with 1 to 2 indentations on either side of the bract. Secondary bracts are elliptic and have entire margins.

*Color.*—The flower bracts of "Bright Red Freedom" are brighter than those of its parent "490", because of less "blue" tones. Upper side — Bright red, between R.H.S. 45A-B. Under side — Red, near R.H.S. 47B.

Flowers: Generally 15–21 cyathia (flowers) were present when the plant was in full bloom. Each cyanthium is about 8 mm long and 6 mm wide, green in color, and fringed with light red at the distal end. A yellow nectar cup protrudes from the side of each cyanthium. The flower pedicel is also green and about 5–6 min in length. The stamens protruding from the cyathia are red. The anthers are bifurcate; the pollen is yellow and copious. The stigmas are red and trifurcate. Cyathia retention was about three weeks beyond the time the flower was fully mature.

*Nectar exudate.*—Present, abundant.

*Seed formation.*—Self-incompatible.

*Fertility.*—Not observed.

What is claimed is:

1. A new amd distinct Poinsettia plant, substantially as herein shown and described, distinguished by its early flowering, bright red flower bracts, dark green foliage and self branching traits.

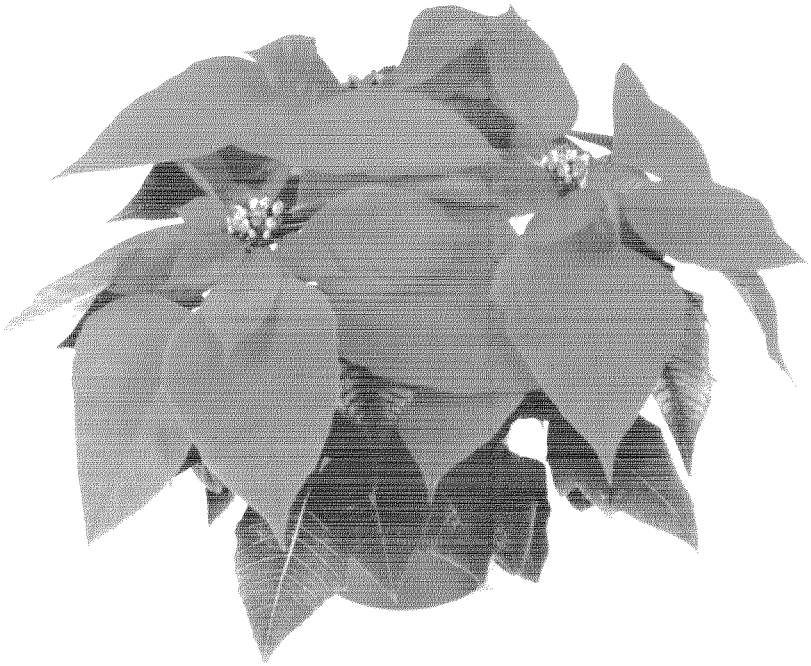
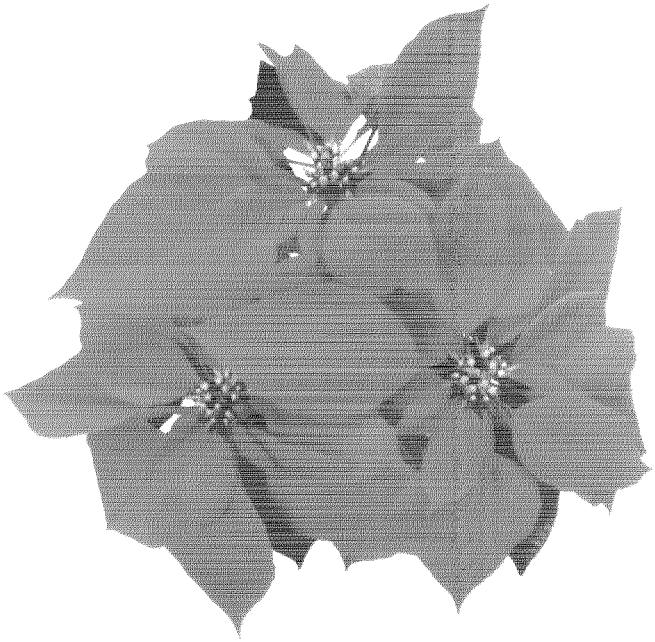

* * * * *